United States Patent
Wheeler, IV et al.

(10) Patent No.: US 8,297,130 B2
(45) Date of Patent: Oct. 30, 2012

(54) MICROTESTING RIG WITH VARIABLE COMPLIANCE LOADING FIBERS FOR MEASURING MECHANICAL PROPERTIES OF SMALL SPECIMENS

(75) Inventors: Robert Wheeler, IV, Hilliard, OH (US); Paul A. Shade, Gallaway, OH (US); Michael D. Uchic, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 551 days.

(21) Appl. No.: 12/617,655

(22) Filed: Nov. 12, 2009

(65) Prior Publication Data

US 2010/0186520 A1 Jul. 29, 2010

Related U.S. Application Data

(60) Provisional application No. 61/113,735, filed on Nov. 12, 2008.

(51) Int. Cl.
*G01N 3/08* (2006.01)
(52) U.S. Cl. ......................................................... 73/818
(58) Field of Classification Search .................... 73/818, 73/760, 571, 781, 833, 826, 856, 816
See application file for complete search history.

(56) References Cited

U.S. PATENT DOCUMENTS

| | | | |
|---|---|---|---|
| 6,574,499 B1* | 6/2003 | Dines et al. | 600/427 |
| 6,938,494 B2* | 9/2005 | Takada et al. | 73/760 |
| 7,056,322 B2* | 6/2006 | Davison et al. | 606/98 |
| 8,107,634 B2* | 1/2012 | Gratzer et al. | 381/59 |

OTHER PUBLICATIONS

M. D. Uchic et al., "Sample dimensions influence strength and crystal plasticity." Science, vol. 305 (2004) 986-989.
G. I. Taylor et al., "The distrotion of crystals of aluminum under compression—part 1." Proc. Royal Soc. Lond. A. vol. 111 (1926) 529-551.
M. D. Uchic et al., "Application of micro-sample testing to study fundamental apsects of plastic flow," Scripta Mater. vol. 54 (2006) 759-764.
J. G. Sevillano et al., "Intrinsic size effects in plasticity by dislocation glide," Mater. Sci. Eng. A, vol. 309-310 (2007) 393-405.
M. Zaiser et al., "Self-affine surface morphology of plastically deformed metals," Phys. Rev. Lett. vol. 93 (2004) 195507.1-195507.4.
J. Weiss and Marsan, D., "Three-dimensional mapping of dislocation avalanches: clustering and space/time coupling," Science, vol. 299 (2003) 89-92.
M.-C. Miguel et al., "Intermittent dislocation flow in viscoplastic deformation," Nature, vol. 410 (2001) 667-671.
P. Sammonds, "Plasticity goes supercriticial," Nature Mater. vol. 4 (2005) 425-426.

(Continued)

*Primary Examiner* — Jewel V Thompson
(74) *Attorney, Agent, or Firm* — AFMCLO/JAZ; Chastity Whitaker

(57) ABSTRACT

The present invention provides a microtesting rig for measuring mechanical properties of small specimens. The rig includes a microsized specimen positioned on a mounting block, an interchangeable contact tip connected with an actuator and configured for contact with the microsized specimen, and a magnifying imaging system for imaging the microsized specimen. The contact tip may be a fiber platen for compression testing or a fiber grip for tension testing.

10 Claims, 7 Drawing Sheets

OTHER PUBLICATIONS

W. N. Sharpe, Jr. et al., "Effect of specimen size on Young's Modulus and fracture strength of polysilicon," J. Microelectromech. Syst. vol. 10 (2001) 317-326.

M. A. Haque and Saif, M. T. A., "Microscale materials testing using MEMS actuators," J. Microelectromech. Syst. vol. 10 (2001) 146-152.

M. A. Haque and Saif, M. T. A., "Application of MEMS force sensors for in situ mechanical characterization of nano-scale thin films in SEM and TEM," Sens. Actuators. A, vol. 97-98 (2002) 239-245.

I. Chasiotis and Knauss, W. G., "A new microtensile tester for the study of MEMS materials with the aid of atomic force microscopy," Exp. Mech. vol. 42 (2002) 51-57.

H. D. Espinosa et al., "A methodology for determining mecahnical properties of freestanding thin films and MEMS materials," J. Mech. Phys. Solids vol. 51 (2003) 47-67.

D. M. Dimiduk et al., "Size-affected single-slip behavior of pure nickel microcrystals," Acta Mater. vol. 53 (2005) 4065-4077.

M. D. Uchic and Dimiduk, D. M., "A methodology to investigate size scale effects in crystalline plasticity using uniaxial compression testing," Mater. Sci Eng. A., vol. 400-401 (2005) 268-278.

J. R. Greer et al., "Size dependence of mechanical properties of gold at the micron scale in the absence of strain gradients," Acta Mater. vol. 53 (2005) 1821-1830.

S. J. Polasik, "Accelerated assessment and representation of materials behavior via integrated electron-optical, focused ion beam and MEMS-based characterization methods," Thesis presented to the Graduate School of the Ohio State University (2005) 101 pages total.

B. H. Kim et al., "Micro electrochemical milling," J. Micromech. Microeng. vol. 15 (2005) 124-129.

Q. Feng et al., "Femtosecond laser micromachining of a single-crystal superalloy," Scripta Mater. vol. 53 (2005) 511-516.

J.-M. Breguet et al., "The laboratory in scanning electron microscope concept: lab-in-SEM," Mechatronics and Robotics, Aachen, Germany (2004) 6 pages total.

D. M. Dimiduk et al., "Overview of experiments on microcrystal plasticity in FCC-derivative materials: selected challenges for modelling and simulation of plasticity," Model Sim. Mater. Sci. Eng. vol. 15 (2007) 135-146.

D. M. Dimiduk et al., "Scale-free intermittent flow in crystal plasticity," Science, vol. 312 (2006) 1188-1190.

* cited by examiner

MICROTESTING RIG WITH VARIABLE COMPLIANCE LOADING FIBERS FOR MEASURING MECHANICAL PROPERTIES OF SMALL SPECIMENS

CROSS-REFERENCE TO RELATED APPLICATION

The present application relates to and claims priority to U.S. Provisional Patent Application No. 61/113,735 filed Nov. 12, 2008. The contents of U.S. Provisional Patent Application No. 61/113,735 are hereby incorporated by reference.

RIGHTS OF THE GOVERNMENT

The invention described herein may be manufactured and used by or for the Government of the United States for all governmental purposes without the payment of any royalty.

FIELD OF THE INVENTION

The present invention relates generally to an improved mechanism that enables quantitative mechanical testing of microsized samples by introducing variable lateral constraints imposed by the lateral stiffness of the testing device. More particularly, the invention employs a flexible fiber or other highly compliant structure that can support a contacting tip for both tensile and compressive test modes.

BACKGROUND OF THE INVENTION

The measurement of mechanical behavior in very small samples, whose dimensions are on the order of microns and below, can offer advantages over conventional macroscopic testing in many instances. Motivations for investigating materials at this length scale include seeking information about size dependent properties in monolithic materials, studying local variation in properties throughout a microstructure, and measuring the mechanical response of fabricated structures that have small dimensions.

In 2004, a study reported on the flow behavior of microscale metallic samples tested in compression using a nanoindenter equipped with a flat tip diamond indenter. The lateral stiffness in these systems was fixed at a value near 0.01 N/µm. Cylindrical specimens were machined using a focused ion beam (FIB) instrument, and tests were conducted under uniaxial loading conditions similar to those practiced at the bulk scale. These ex-situ micro-scale tests are affected by some of the same undesired influences as experienced in bulk compression tests. One such influence is the platen-sample friction for which there has been no attempt to address in the micro-scale tests. The importance of frictional forces on compression testing of single crystals was first noted in 1926 where both flow stress properties and local physical sample deformation were greatly influenced by the addition of a lubricant to the platen-sample interface.

There exists a need for a system and method that enables testing of microsized samples by introducing variable lateral constraints imposed by the lateral stiffness of the testing device.

SUMMARY OF THE INVENTION

In work leading up to the present invention, a device was designed and constructed to allow the measurement of deformation properties in micron-sized specimens while simultaneously recording high resolution electron images within a scanning electron microscope (SEM) or dual beam focused ion beam (DBFIB). This in-situ testing device is capable of mechanical testing in both compression and tension and has been fitted with appropriately machined contact tips composed of single crystal diamond or novel, compliant fibers of the present invention.

The present invention provides a device designed and constructed to allow the quantitative measurement of deformation properties in micron-sized specimens while imparting an exceedingly small constraining force to the deforming body. Ex-situ test methodologies can provide high precision data that relate quantitative stress and strain response during deformation. The present invention provides an alternative in-situ testing approach that also employs simultaneous electron imaging of very small test specimens within a scanning electron microscope (SEM) or dual beam focused ion beam (DBFIB) during the deformation experiment. These images are used to correlate the stress-strain data with the spatial and temporal nature of deformation-induced flow and fracture events that develop during the course of a test. Real time imaging facilitates the operation of tests on micro-samples that rely on complex set-ups, such as the alignment of tension grips about very small free-standing specimens.

The present invention incorporates a high precision piezo-electric actuator, a high precision inertial force positioning stage, a small, low profile load cell and a variety of highly compliant contact platens and grips that can be manufactured from a SiC or similar compliant fiber. Displacement along the specimen gauge length is measured directly from the images. Both compression and tension experiments have been conducted on microsized samples fabricated from bulk material using the DBFIS. These specimens are fabricated to elicit the simple stress states afforded by uniaxial loading of standard geometric shapes (e.g. round pillars, rectangular "dog bone" plates, etc.).

The present invention is beneficial for research studies or characterizations of materials where mechanical properties of very small structures will be investigated. These structures might be representative small volumes of material extracted from a larger bulk specimen or they might be fabricated from intrinsically small features within a complex device or assembly. The common factor in the application of this invention is that the size scale of the cross sectional area in the tested specimen is on the order of tens of square microns or smaller. Due to the small size of these test specimens, some form of magnifying imaging system must be available such as an optical microscope, scanning electron microscope or focused ion beam microscope. The physical device described in this invention must then be incorporated with the appropriate microscope during the facilitation of measurements.

Some examples of technologies and materials where this invention might be useful include thin films, microelectromechanical systems (MEMS), composite materials, welding or joining applications, and generally all fundamental studies of materials deformation.

Construction of the microtesting rig in the invention offers certain advantages over the current technology available for microscale mechanical testing. While the lateral stiffness in nanoindenter systems is fixed at some intermediate value, they are not specifically designed to be excessively stiff. This methodology also currently employs only diamond contact tips, which are intrinsically very stiff. Thus, lateral contact stiffness in these systems is limited to the intermediate lateral stiffness intrinsic to the load train into which the diamond is mounted. The high-end lateral stiffness, for the present invention, is much greater at 0.1 N/µm. This enables microscale mechanical testing under new, higher stiffness conditions.

The fiber can be used to control the lateral stiffness for microscale testing. Fibers of varying length, diameter, and composition can be used to affect the properties in the fiber contact and thereby control lateral stiffness at the sample/fiber contact. This enables microscale mechanical testing under new, ultra-low stiffness conditions.

The concept of variable contact tips possessing different properties is new and allows a range of imposed lateral stiffness conditions for an experiment. The device in this invention begins with a high natural system stiffness, by design, and thus offers a wide range in potential lateral stiffness during testing.

Other laterally compliant components, such as springs, can be employed to support the contact tip within this invention. This could have the platen or grip machined as part of the component or it could be an intermediate element onto which a tip could be attached. The laterally compliant contact tip concept can also be applied to the nanoindenter methodology in place of the standard diamond platen.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION utilizes a compliant fiber within an existing testing frame used to investigate deformation behavior of microsized specimens. Initially, compression tests were conducted using the test system equipped with a diamond platen (without a compliant fiber). Test results differed from ex-situ results conducted using a nanoindenter. It was contemplated that lateral stiffness in the system was the likely source of these differences. This problem was overcome by the use of a fiber to allow testing of appropriately fabricated samples in tension. A fixed grip was designed and cut into the free end of a fiber using the focused ion beam microscope. A compliant SiC fiber was chosen, which would allow for minor self alignment of the grip during initial application of load to the microsamples and would accommodate lateral movements induced by deforming specimens. The SiC fiber was chosen for the grip application because of the high stiffness along its length and low stiffness perpendicular to the length in cases where the length is several millimeters or greater. A similar SiC fiber was machined for compression testing in order to remove the lateral constraints on the deforming sample in this test. These tests produced yield and plastic flow data more closely resembling the ex-situ nanoindenter data, confirming the influence of lateral stiffness on microscale mechanical tests.

Figure 1:
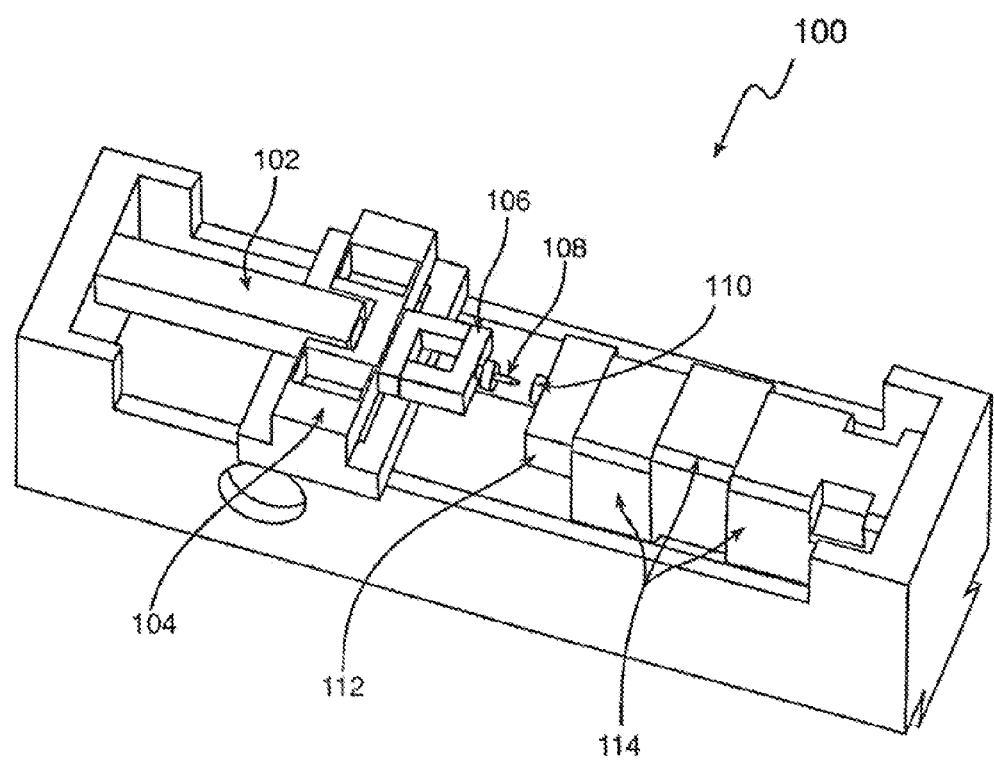
FIG. 1 illustrates an in-situ micromechanical testing rig of the present invention.

Referring now to the drawings in which like reference designators refer to like elements, FIG. 1 presents a schematic illustration of the test frame 100 that can be placed on the stage of an SEM microscope. It is equipped with a piezoelectric actuator 102 for fine displacement control at the subnanometer level. An alignment fixture/flexor 104 is employed between the actuator 102 and a low range load cell 106 to ensure axial loading. The load sensitivity may be, for example, 10 milligrams. As FIG. 1 illustrates, the compression platen or tensile grip 108 is attached to the load cell 106. A specimen 110 is located on a mounting block 112, which is positioned on an XYZ piezoelectric stick-slip positioning stage 114. Importantly, the setup allows the exchange of various compression platens and tension grips 108.

Compression platens 108 composed of diamond crystal and novel SiC fiber were evaluated and compared. The diamond platen was prepared from a 1 mm long and 0.5 mm wide diamond crystal with a tapered end. The tip was prepared by mechanical grinding followed by FIB cutting to produce a 40 μm×40 μm flat surface perpendicular to the loading axis. Similarly, a second tip was prepared from a SiC fiber 8 mm in length by 0.1 mm in diameter, with the contact surface again being prepared by FIB. The 80:1 aspect ratio of the SiC fiber platen enables the lateral stiffness to be very low, measured to be less than 0.0001 N/μm. By comparison, the diamond platen has a high lateral stiffness, measured to be ~0.1 N/μm.

In operation, the specimens 110 to be tested are positioned as shown in FIG. 1 and are mounted on the XYZ positioning stage 114. A mounting block 112 may be positioned between the specimen 110 and the positioning stage 114. Alternatively, the mounting block 112 and positioning stage 114 may be a unitary structure (i.e. the mounting block 112 may be part of, or integrated into, the positioning stage). The stage 114 bases its movement on a piezoelectric inertial force mechanism that provides nanometer scale positioning resolution with zero backlash. Further, it supports loads up to 1 N in a small footprint that is also vacuum compatible. The specimens 110 described herein were machined from the near edge region of a bulk sample. This allowed imaging of pillars during deformation from an orientation perpendicular to the specimen 110 and loading axis. Tests were conducted in a quasi-static mode, in which the specimen 110 undergo sequential periods of first loading and then holding for image collection. This process was automated using custom software. Displacements were calculated from the image data by tracking the motion of fiducial markers machined into the surface of the specimen 110. These displacements are correlated with load data collected throughout the experiment to construct load-displacement or stress-strain curves (FIG. 6).

In more detail, the procedure for conducting a mechanical test in the microtesting rig 100 begins with selection of a contacting tip 108 for the desired test and placing that tip 108 adjacent the load cell 106. The bulk specimen 110 on which the test sample has been fabricated is then placed within the test frame 100. The XYZ positioning stage 114 is then employed to align the specimen 110 with the platen or grip 108.

Figure 2:
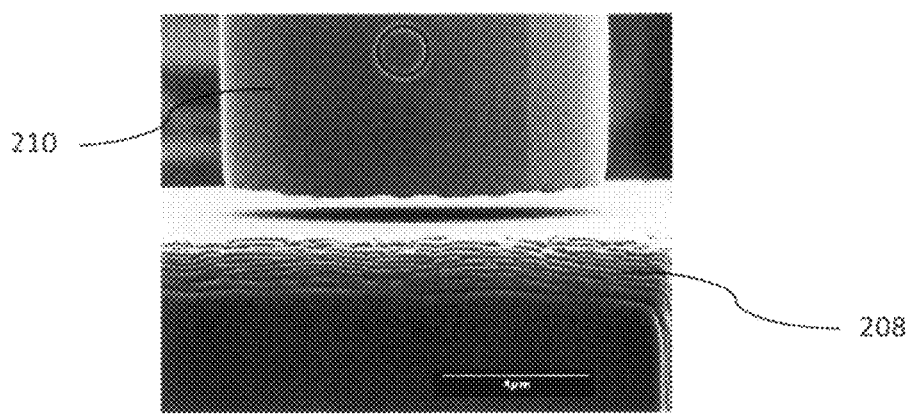
FIG. 2 is a scanning electron microscope (SEM) image showing a compression specimen and a fiber platen of the present invention.

FIG. 2 illustrates the close approach of a round compression pillar 210 with the flat tip platen end of a SiC fiber 208, which remains stationary during this procedure. When minimal contact is made between the sample 210 and the platen 208, the positioning stage 114 (FIG. 1) is placed in a stationary state. All subsequent loading of the sample 210 is accomplished through the load train of the test rig 100 (FIG. 1) composed of the piezoelectric actuator 102 (FIG. 1), the alignment flexor 104 (FIG. 1), the load cell 106 (FIG. 1), and the platen/grip 208.

Figure 3A:
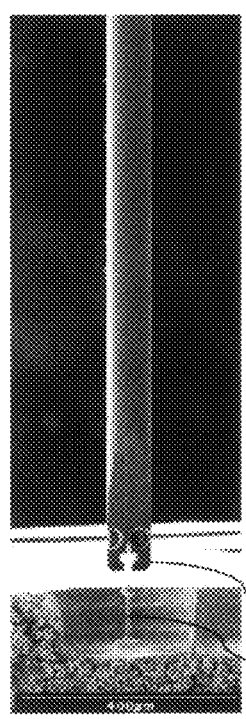
FIGS. 3A and 3B are SEM images showing a tension specimen aligned close to a fiber grip of the present invention and the tension specimen positioned in the fiber grip, respectively.
Figure 3B:
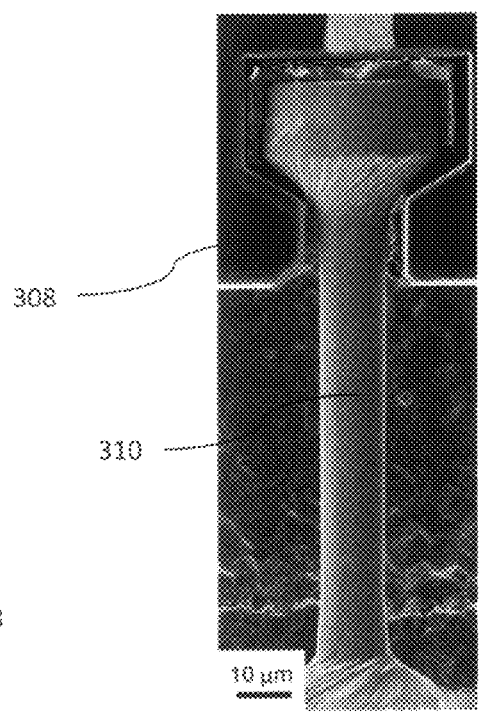

FIG. 3A shows a tension specimen 310 positioned near the SiC grip 308, and FIG. 3B shows the tension specimen 310 positioned within the SiC grip 308. After positioning the specimen 310 relative to the grip or platen 308, loading of the specimen 310 occurs by displacement of the load train 106 (FIG. 1) via the actuator 102 (FIG. 1). Quantitative measurement of stress and strain require uniaxial loading of the specimens 310.

Figures 4A, 4B:
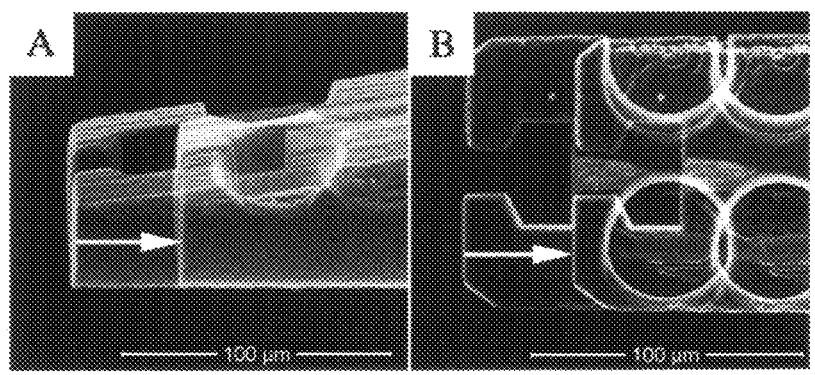
FIGS. 4A and 4B are SEM images showing axial travel in the load train viewed at the grip with the microtesting rig tilted 70 degrees from the electron beam (FIG. 4A) and normal to the electron beam (FIG. 4B)

FIGS. 4A and 4B illustrate the travel of the tension grip over the entire 40 micron stroke range of the current actuator. By viewing from the two orientations (FIGS. 4A and 4B), it is evident that no lateral translations are present, which might influence the deformation response of a microsample being tested. This observation confirms the uniaxial travel of the contact tip.

Since numerous studies have been conducted in recent years employing the compression testing capabilities of the nanoindenter, it is most illustrative to consider the compressive response of a series of representative samples. These were tested with both the diamond (high lateral stiffness) and SiC fiber (low lateral stiffness) compression platens. The material chosen for this investigation was Rene N5, a single crystal, Ni-based superalloy commonly used in turbine blade applications. The bulk sample was oriented to give a <123> single slip compression axis. Further, the sample was oriented such that the viewing direction during testing would be <−1 −1 1>, which places the primary displacement vector in the imaging plane. Compression samples were prefabricated using micro-electrodischarge machining (micro-EDM) and finished using FIB based ion lathe milling. All samples were nominally 10 µm in diameter with a 2.3:1 length to diameter aspect ratio.

Figure 5:
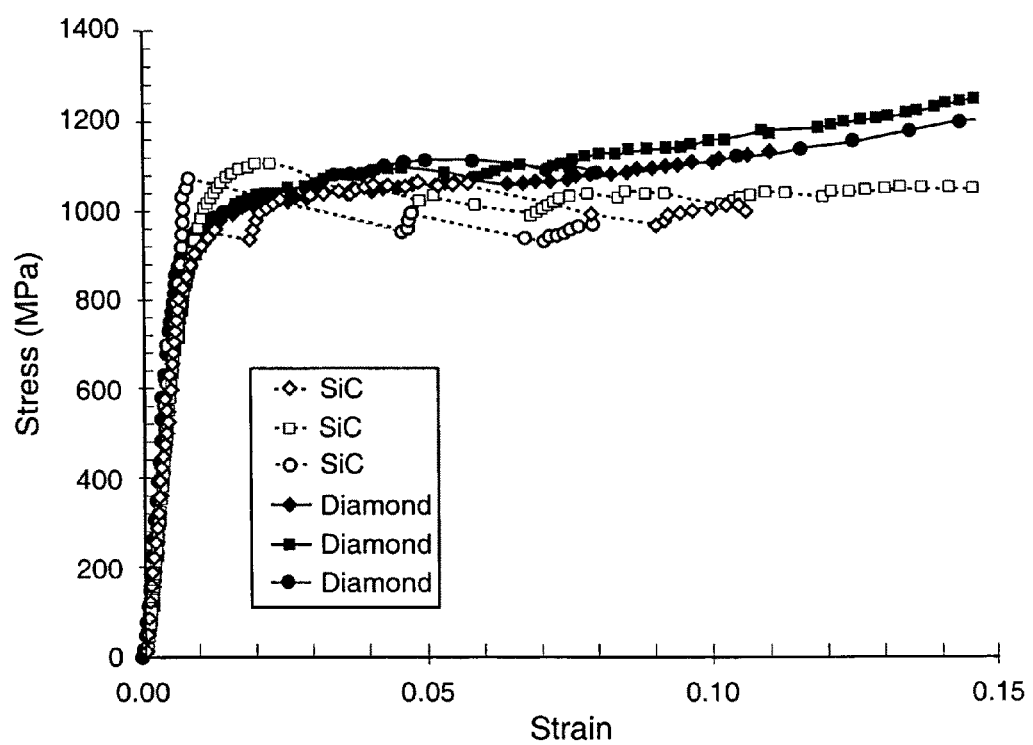
FIG. 5 is a graph showing flow curves for a compression test of a nickel base superalloy specimen using a diamond platen and a fiber platen.

The flow curves of three tests each are shown for the diamond and SiC fiber platens in FIG. 5. The response of the diamond-tested specimens (red data) is characterized by smooth elastic loading followed by a gradual transition to plastic flow, which then indicates a generally steady work hardening regime. The flow curves for the tests conducted with the SiC fiber are quite different. These curves (blue data) are marked by sharp stress drops, which are associated with strain bursts. After yielding at a somewhat higher stress level than the diamond test samples, a series of serrations in the stress-strain curves follow. Here, the flow stress remains relatively low when compared with the initial yield value. The flow behavior in the SiC fiber platen test does not show any overall work hardening even to strains exceeding 10 percent.

Figures 6A, 6B:
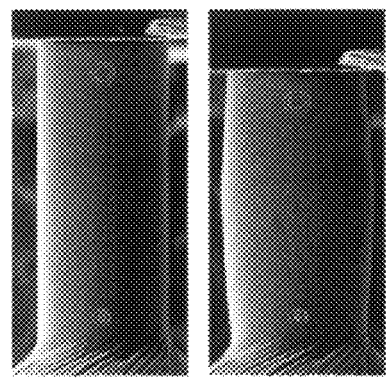
FIGS. 6A and 6B show SEM images of a specimen prior to and after a diamond platen compression test, respectively.

The physical changes in shape for samples tested with the two compression platens are illustrated in FIGS. 6 and 7. The images of the diamond platen case show a Rene N5 single crystal pillar prior to compression (FIG. 6A) and after compression to ten percent strain (FIG. 6B). The sample indicates essentially uniaxial displacement of the top of the specimen, in contact with the platen, relative to the base. The large and small circles act as fiducial indicators for displacement measurement. Plastic flow in the sample during compression is uniformly distributed across the specimen length and results in general barreling of the starting cylindrical geometry. This results from the high, lateral stiffness of the test frame with the diamond platen in place. The diamond restrains lateral movement of the sample/platen contact, which would be promoted by the single slip, <123> crystallographic orientation established in this test.

Figures 7A, 7B:
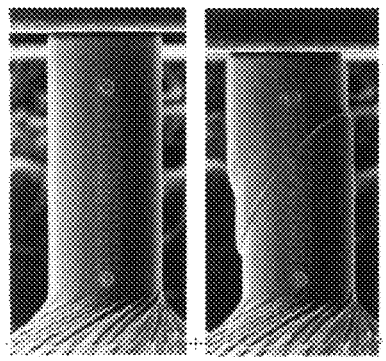
FIGS. 7A and 7B show SEM images of a specimen prior to and after a fiber platen compression test, respectively.

In an identical test performed with a SiC fiber platen in place, results from the change in shape during plastic flow are displayed in FIGS. 7A and 7B. Here, the deformed specimen geometry is quite different and shows very discrete localized plastic flow. The local slip steps result in a net lateral displacement of the top part of the specimen at the sample/platen contact. This is clearly noted by the sharp discontinuity in the triple row of vertically aligned reference points. (FIG. 7B). The slip localization is responsible for the lack of barreling found when the diamond platen was employed. In the case of the SiC fiber platen, the lateral movement associated with slip on the inclined primary slip plane is not inhibited. Thus, sample material in contact with the SiC platen is free to flow as dictated by the crystal orientation.

The resultant, deformed specimen shape is consistent with observations made on similar materials tested with the nanoindenter. In this case, the more compliant test frame into which the diamond platen is mounted is responsible for the available lateral movement. The lateral stiffness of the MTS NanoXP nanoindenter commonly used in ex-situ testing of micropillars is given by the manufacturer to be about 0.01 N/µm. Measurements made on the two platens employed in the present invention indicate a lateral stiffness of 0.1 N/µm for the diamond platen and less than 0.0001 N/µm for the SiC fiber platen.

It should be noted that the invention described herein provides easy control over the lateral stiffness of the load train by simply exchanging contact platens. The remaining elements of the test frame compose a system with very high lateral stiffness. This is further evidenced by the ability of the diamond indenter to completely suppress lateral movement in a high strength sample, having common microsample dimensions, oriented to exhibit large lateral movement upon plastic flow.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A microtesting rig for measuring mechanical properties of small specimens, comprising:
    a mounting block configured to receive a microsized specimen;
    an actuator configured to generate a displacement motion of at least 10 µm; and
    a compression contact tip operably coupled to the actuator and configured to apply a compressive force onto the microsized specimen, the compressive force having a magnitude proportional to the displacement motion of the actuator; and
    a tension grip, interchangeable with the compression contact tip to be operably coupled to the actuator, the tension grip configured to receive at least a portion of the microsized specimen and apply a tensioning force thereto, the tensioning force having a magnitude proportional to the displacement motion of the actuator.

2. The microtesting rig of claim 1, wherein the contact tip, the tension grip, or both comprises a fiber.

3. The microtesting rig of claim 2, wherein the fiber platen is a SiC fiber.

4. The microtesting rig of claim 1, further comprising:
a load cell positioned between the actuator and the contact tip or tension grip.

5. The microtesting rig of claim 4, further comprising:
an alignment flexor positioned between the actuator and load cell.

6. The microtesting rig of claim 1, further comprising:
an XYZ positioning stage operably coupled to the mounting block.

7. A method of using the microtesting rig of claim 1 for tension testing, the method comprising:
mounting a microsized specimen onto the mounting block;
coupling the tension grip to the actuator;
loading a portion of the microsized specimen to the tension grip;
actuating the actuator generate the displacement motion;
with an imaging system, capturing a plurality of images of the tensioned microsized specimen during the displacement motion; and
with the captured plurality of images, calculating displacements of the tensioned microsized specimen.

8. The method of claim 7, wherein the imaging system is a scanning electron microscope.

9. The method of claim 7, wherein the imaging system is a dual beam focused ion beam.

10. A system for evaluating plastic flow in a microsized specimen having a width dimension less than 40 µm the system comprising:
a high-magnification imaging device comprising:
a stage configured to receive a sample: and
a camera configured to capture images of a sample on the stage: and
a microtesting rig comprising:
a frame configured to be mounted to the stage of the high-magnification imaging device;
a mounting block operably coupled to the frame and configured to receive a microsized specimen;
an actuator operably coupled to the frame and configured to generate a displacement motion of at least 10 µm in a direction toward the mounting block; and
a plurality of actuator tips, each of the plurality of actuator tips being interchangeably coupled to the actuator and configured to contact the microsized specimen mounted onto the mounting block, wherein a first one of the plurality of actuator tips is configured to apply a compressive force onto the microsized specimen and a second one of the plurality of actuator tips is configured receive at least a portion of the microsized specimen and apply a tensioning force thereto.

* * * * *